(12) United States Patent
Lamb et al.

(10) Patent No.: US 11,617,903 B2
(45) Date of Patent: Apr. 4, 2023

(54) SYSTEM AND METHOD FOR RESPIRATORY GATED RADIOTHERAPY

(71) Applicant: The Regents of The University of California, Oakland, CA (US)

(72) Inventors: James M. Lamb, Los Angeles, CA (US); John S. Ginn, Los Angeles, CA (US); Daniel A. Low, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 474 days.

(21) Appl. No.: 16/634,308

(22) PCT Filed: Jul. 31, 2018

(86) PCT No.: PCT/US2018/044475
§ 371 (c)(1),
(2) Date: Jan. 27, 2020

(87) PCT Pub. No.: WO2019/027947
PCT Pub. Date: Feb. 7, 2019

(65) Prior Publication Data
US 2020/0238102 A1    Jul. 30, 2020

Related U.S. Application Data

(60) Provisional application No. 62/538,854, filed on Jul. 31, 2017.

(51) Int. Cl.
*A61N 5/10* (2006.01)
*G16H 20/40* (2018.01)
(Continued)

(52) U.S. Cl.
CPC .............. *A61N 5/1068* (2013.01); *A61B 6/02* (2013.01); *A61N 5/1039* (2013.01); *G16H 20/40* (2018.01);
(Continued)

(58) Field of Classification Search
CPC ............................ A61N 5/1068; G16H 20/40
(Continued)

(56) References Cited

U.S. PATENT DOCUMENTS 9,248,312 B2    2/2016  Li
2005/0187464 A1 *  8/2005  Ho ...................... A61B 5/7285
600/428
(Continued)

OTHER PUBLICATIONS

Yang, Y., et al, Longitudinal diffusion MRI for treatment response assessment: Preliminary experience using an MRI-guided tri-cobalt 60 radiotherapy system. Med Phys. 2016;43:1369-1373.
(Continued)

*Primary Examiner* — Thomas J Lett
(74) *Attorney, Agent, or Firm* — Quarles & Brady LLP

(57) ABSTRACT

A system and method is provided for magnetic resonance imaging (MRI) guided respiratory gated radiotherapy using a respiratory motion model. MRI-guided respiratory gating is performed with a continuously updated model that represents a patient's internal anatomy as a mathematical function of an external respiratory surrogate. The motion model may be built and updated by acquiring images of a tissue in a subject and measuring, using the images, a position of the tissue in the images to determine motion of the tissue. The surrogate respiratory signal is acquired contemporaneously with acquiring the images. Motion of the tissue and the surrogate respiratory signal are correlated to create the motion model for the subject and gating a radiotherapy system may then be based upon the motion
(Continued)

model. A multi-planar model-based respiratory gating may also be performed by sequentially imaging a stack of adjacent slice positions.

23 Claims, 8 Drawing Sheets

(51) Int. Cl.
  G16H 50/50    (2018.01)
  G16H 30/40    (2018.01)
  A61B 6/02     (2006.01)
(52) U.S. Cl.
  CPC ............. *G16H 30/40* (2018.01); *G16H 50/50* (2018.01); *A61N 2005/1055* (2013.01)
(58) Field of Classification Search
  USPC .......................................................... 600/1
  See application file for complete search history.

(56) References Cited

U.S. PATENT DOCUMENTS

| | | | |
|---|---|---|---|
| 2009/0180589 | A1 | 7/2009 | Wang |
| 2012/0310053 | A1* | 12/2012 | Henning ................ A61B 6/527 600/407 |
| 2012/0310079 | A1* | 12/2012 | Henning ................ A61B 6/503 600/407 |
| 2013/0187649 | A1 | 7/2013 | Bhat |
| 2014/0146936 | A1 | 5/2014 | Liu et al. |
| 2016/0310761 | A1* | 10/2016 | Li ......................... A61N 5/1039 |
| 2018/0161599 | A1* | 6/2018 | Yue ...................... A61N 5/1039 |
| 2019/0110784 | A1* | 4/2019 | Nawana .................. G16H 40/40 |
| 2019/0113587 | A1* | 4/2019 | Paulson ............. G01R 33/4808 |

OTHER PUBLICATIONS

Yun, J., et al, First demonstration of intrafractional tumor-tracked irradiation using 2D phantom MR images on a prototype linac-MR. Med Phys. 2013;40:051718.

Zhao, T. "A free-breathing lung motion model." (2010). All Theses and Dissertations (ETDs). 400.

European Patent Office. Extended European Search Report for application 18841177.1. dated Jun. 10, 2021. 9 pages.

Ginn, J. S., et al. "Model-interpolated gating for magnetic resonance image-guided radiation therapy." International Journal of Radiation Oncology Biology Physics 102.4 (2018): 885-894.

Baumgartner, C.F. et al, "Autoadaptive motion modelling for MR-based respiratory motion estimation," Medical Image Analysis 35, 83-100 (2017).

Bjerre, T., et al, Three-dimensional MRI-linac intra-fraction guidance using multiple orthogonal cine-MRI planes. Phys Med Biol. 2013;58:4943-4950.

Bourque, A.E., et al, A particle filter motion prediction algorithm based on an autoregressive model for real-time MRI-guided radiotherapy of lung cancer. Biomed Phys Eng Expr. Apr. 24, 2017;3:035001.

Cervino, L.I., et al, MRI-guided tumor tracking in lung cancer radiotherapy. Phys Med Biol. 2011;56:3773-3785.

Chung, Y.E., et al, Varying appearances of cholangiocarcinoma: Radiologic-pathologic correlation. Radiographics. 2009;29:683-700.

Crijns, S.P., et al, Proof of concept of MRI-guided tracked radiation delivery: Tracking one-dimensional motion. Phys Med Bio. 2012;57:7863-7872.

Crijns, S.P., et al, Towards MRI-guided linear accelerator control: Gating on an MRI accelerator. Phys Med Biol. 2011;56:4815-4825.

Dou, T.H., et al, A method for assessing ground-truth accuracy of the 5dct technique. Int J Radiat Oncol Biol Phys. 2015;93:925-933.

Freedman, J.N., et al, T2-weighted 4D magnetic resonance imaging for application in magnetic resonance guided radiotherapy treatment planning. Invest Radiol. Apr. 28, 2017;52:563-573.

Fu, D., et al, Xsight lung tracking system: A fiducial-less method for respiratory motion tracking. in: Treating Tumors that Move with Respiration. 1. Springer, Berlin, Heidelberg; 2007:265.

Ginn, J.S., et al, Characterization of spatial distortion in a 0.35 t mri-guided radiotherapy system. Phys Med Biol. Apr. 20, 2017;62:4525-4540.

Giraud, P., et al, Reduction of organ motion in lung tumors with respiratory gating. Lung Cancer. 2006;51:41-51.

Griswold, M.A., et al, Generalized autocalibrating partially parallel acquisitions (GRAPPA). Magn Reson Med. 2002;47:1202-1210.

Harris, W. et al, "A Technique for Generating Volumetric Cine-Magnetic Resonance Imaging," Int J Radiat Oncol Biol Phys 95, 844-853 (2016).

Harris, W. et al, "Accelerating volumetric cine MRI (VC-MRI) using undersampling for real-time 3D target localization/tracking in radiation therapy: a feasibility study," Physics in Medicine & Biology 63, 01NT01 (Dec. 2017).

International Searching Authority, International Search Report and Written Opinion for application PCT/US2018/044475, dated Oct. 4, 2019.

Keall, P.J., et al, The management of respiratory motion in radiation oncology report of AAPM task group 76. Med Phys. 2006;33:3874-3900.

Kilby, W., et al, The cyberknife robotic radiosurgery system in 2010. Technol Cancer Res Treat. 2010;9:433-452.

King, A.P., et al, Thoracic respiratory motion estimation from MRI using a statistical model and a 2D image navigator. Med Image Anal. 2012;16:252-264.

Klein, S., et al, Adaptive stochastic gradient descent optimisation for image registration. Int J Comp Vis. 2009;81:227.

Klein, S., et al, Elastix: A toolbox for intensity-based medical image registration. IEEE Trans Med Imaging. 2010;29:196-205.

Lamb, J.M., et al, Dosimetric validation of a magnetic resonance image gated radiotherapy system using a motion phantom and radiochromic film. Journal of applied clinical medical physics. Apr. 2017;18:163-169.

Lee, D., et al, Audiovisual biofeedback improves the correlation between internal/external surrogate motion and lung tumor motion. Med Phys. 2018;45:1009-1017.

Li, G. et al, "Novel Super-Resolution Approach to Time-Resolved Volumetric 4-Dimensional Magnetic Resonance Imaging With High Spatiotemporal Resolution for Multi-Breathing Cycle Motion Assessment," International Journal of Radiation Oncology*Biology*Physics 98, 454-462 (Jun. 2017).

Liu, Y., et al, T2-weighted four dimensional magnetic resonance imaging with result-driven phase sorting. Med Phys. 2015;42:4460-4471.

Loo, B.W. Jr., et al, Motion management and image guidance for thoracic tumor radiotherapy: Clinical treatment programs. Fron Radiat Ther Oncol. 2011;43:271-291.

Low, D.A., et al, Novel breathing motion model for radiotherapy. Int J Radiat Oncol Biol Phys. 2005;63:921-929.

Maetani, Y., et al, MR imaging of intrahepatic cholangiocarcinoma with pathologic correlation. AJR Am J Roentgenol. 2001;176:1499-1507.

Mahmood, F., et al, Repeated diffusion MRI reveals earliest time point for stratification of radiotherapy response in brain metastases. Phys Med Biol. Mar. 2017;62:2990-3002.

McClelland JR, et al. 4d motion models over the respiratory cycle for use in lung cancer radiotherapy planning. Medical Imaging. SPIE. 2005. pp. 11.

McClelland, J.R., et al, Respiratory motion models: A review. Med Image Anal. 2013;17:19-42.

Mutic, S., et al. The viewray system: Magnetic resonance guided and controlled radiotherapy. Semin Radiat Oncol. 2014;24:196-199.

O'Connell, D.P., et al, Comparison of breathing gated ct images generated using a 5dct technique and a commercial clinical protocol in a porcine model. Medical Physics. 2015;42:4033-4042.

Pepin, E.W., et al, Correlation and prediction uncertainties in the cyberknife synchrony respiratory tracking system. Med Phys. 2011;38:4036-4044.

(56) References Cited

OTHER PUBLICATIONS

Santelli, C., et al, Respiratory bellows revisited for motion compensation: Preliminary experience for cardiovascular MR. Magn Reson Med. 2011;65:1097-1102.

Savitzky, A., et al. Smoothing and differentiation of data by simplified least squares procedures. Anal Chem. 1964;36:1627-1639.

Sawant, A., et al, Management of three-dimensional intrafraction motion through real-time DMLC tracking. Med Phys. 2008;35:2050-2061.

Scheffler, K., et al. Principles and applications of balanced SSFP techniques. Eur Radiol. 2003;13:2409-2418.

Seregni, M. et al, "Motion prediction in MRI-guided radiotherapy based on interleaved orthogonal cine-MRI," Phys Med Biol 61, 872-887 (2016).

Shamonin, D.P., et al, Fast parallel image registration on CPU and GPU for diagnostic classification of Alzheimer's disease. Front Neuroinform. 2014;7:50.

Sharp, G.C., et al, Prediction of respiratory tumour motion for real-time image-guided radiotherapy. Phys Med Biol. 2004;49:425-440.

Shaverdian, N., et al, Feasibility evaluation of diffusion-weighted imaging using an integrated MRI-radiotherapy system for response assessment to neoadjuvant therapy in rectal cancer. Br J Radiol. Feb. 2017;90:20160739.

Shirato, H., et al, Physical aspects of a real-time tumor-tracking system for gated radiotherapy. Int J Radiat Oncol Biol Phys. 2000;48:1187-1195.

Slotman, B.J., et al, 4D imaging for target definition in stereotactic radiotherapy for lung cancer. Acta Oncol. 2006;45:966-972.

Smith, W.L., et al. Time delays in gated radiotherapy. J Appl Clin Med Phys. 2009;10:2896.

Stemkens, B. et al, "Image-driven, model-based 3D abdominal motion estimation for MR-guided radiotherapy," Phys Med Biol 61, 5335-5355 (2016).

Thomas, D. et al. "A novel fast helical 4D-CT acquisition technique to generate low-noise sorting artifact-free images at userselected breathing phases," Int J Radiat Oncol Biol Phys 89, 191-198 (2014).

Torshabi, A.E., et al, Targeting accuracy in real-time tumor tracking via external surrogates: A comparative study. Technol Cancer Res Treat. 2010;9:551-562.

Van der Voort van Zyp, N.C., et al, Stereotactic radiotherapy with real-time tumor tracking for non-small cell lung cancer: Clinical outcome. Radioth Oncol. 2009;91:296-300.

Wagman, R., et al, Respiratory gating for liver tumors: Use in dose escalation. Int J Radiat Oncol Biol Phys. 2003;55:659-668.

* cited by examiner

SYSTEM AND METHOD FOR RESPIRATORY GATED RADIOTHERAPY

CROSS-REFERENCE TO RELATED APPLICATIONS

The present application represents the national stage entry of International Application PCT/US2018/044475, filed Jul. 31, 2018, which claims the benefit of U.S. Provisional Application Ser. No. 62/538,854, filed on Jul. 31, 2017, and entitled "System and Method for Respiratory Gated Radiotherapy Using Low Frame Rate MRI and a Breathing Motion Model." The disclosure of each of the above identified patent applications is incorporated by reference herein.

STATEMENT REGARDING FEDERALLY SPONSORED RESEARCH

N/A

BACKGROUND

Conventional external beam radiation therapy, also referred to as "teletherapy," is commonly administered by directing a linear accelerator (LINAC) to produce beams of ionizing radiation that irradiates the defined target volume in a subject. The radiation beam is a single beam of radiation that is delivered to the target region from several different directions, or beam paths. Together, the determination of how much dose to deliver along each of these beam paths constitutes the so-called radiation therapy "plan." The purpose of the treatment plan is to accurately identify and localize the target volume in the subject that is to be treated.

Intensity modulated radiation therapy (IMRT) is an external beam radiation therapy technique that utilizes computer planning software to produce a three-dimensional radiation dose map, specific to a target tumor's shape, location, and motion characteristics. Various regions within a tumor and within the subject's overall anatomy may receive varying radiation dose intensities through IMRT, which treats a subject with multiple rays of radiation, each of which may be independently controlled in intensity and energy. Each of these rays or beams is composed of a number of sub-beams or beamlets, which may vary in their individual intensity, thereby providing the overall intensity modulation. Because of the high level of precision required for IMRT methods, detailed data must be gathered about tumor locations and their motion characteristics. In doing so, the radiation dose imparted to healthy tissue can be reduced while the dose imparted to the affected region, such as a tumor, can be increased. In order to achieve this, accurate geometric precision is required during the treatment planning stage.

Image-guided radiation therapy (IGRT) employs medical imaging, such as magnetic resonance (MR) or computed tomography (CT), concurrently with the delivery of radiation therapy to a subject undergoing treatment. In general, IGRT is employed to accurately direct radiation therapy using positional information from the medical images to supplement a prescribed radiation delivery plan. The advantage of using IGRT is twofold. First, it provides a means for improved accuracy in delivering radiation fields. Second, it provides a method for reducing the dose imparted to healthy tissue during treatment. Moreover, higher accuracy in delivering radiation fields allows for dose escalation in tumors, without appreciably increasing dose levels to the surrounding healthy tissue. Also, dose escalation allows for treatments to be completed in fewer fractions, creating greater throughput and fewer subject visits.

Forms of active respiratory motion compensation for radiotherapy, consisting of gating or tracking, have been in clinical use for almost two decades. In respiratory gating, the radiation beam is turned on or off based on tumor location and/or respiratory phase. In respiratory tracking, the radiation beam direction is changed based upon the measured or estimated tumor position. Intrafractional variations present additional challenges. In particular, large translations, rotations, and deformations occurring due to respiration, peristalsis, organ filling, or muscle relaxation can cause deviations between the planned and delivered dose. Respiratory gating is one approach to compensate for respiratory motion. On conventional linear accelerators, a one-dimensional motion surrogate signal (e.g. from a respiratory bellows or reflective marker placed on the chest of a patient) is monitored over time. When the signal falls within a pre-determined threshold, the beam is turned on. On state-of-the-art hybrid MR imaging and RT treatment devices, gating can be based on rapidly acquired 2D cross-sectional images intersecting the target and/or organs at risk (OAR). The MR images reduce the uncertainty in estimating target position from motion surrogate signals.

The use of 4D CT or MR imaging (3D+respiratory phase) during simulation can also help to account for intrafraction motion. An internal target volume (ITV) may be created to encompass the total extent of the gross target volume (GTV) throughout the respiratory cycle. The GTV moves within this ITV while the beam is on, resulting in larger irradiated volumes that include OAR.

More recently, the use of pre-beam 4D-MRI has been proposed to be used in conjunction with beam-on cine imaging to accumulate dose on MR-guided RT systems. In this approach, a motion model is generated from the 4D-MRI and dynamically updated throughout the treatment fraction through deformable registration with the cine images. The dynamic update of the motion model facilitates generation of a synthetic 3D volume at the frame rate of the cine images, while also permitting control for deviations from the average respiratory cycle determined from the pre-beam 4D-MRI. While this is a powerful method, it has two key limitations. First, the frame rate of the cine images must be rapid enough to capture respiratory motion, limiting the pulse sequences that can be used and preventing interleaved functional imaging. Second, this method has no provision for validating model accuracy during treatments.

A plethora of methods exist for acquiring 4D-MRI. They can include 2D multi-slice approaches or volumetric (3D) approaches. Most commonly, the data sorting is performed retrospectively. A rapidly emerging 4D-MRI approach is that of a 3D stack-of-stars radial acquisition with a golden angle increment. This technique permits the use of combined parallel imaging and sparsity constraints to reconstruct high quality 3D volumes at multiple respiratory phases from highly undersampled acquisitions with durations under 2 minutes.

If the use of deformable registration is to be avoided, dynamically updating 4D-MRIs must be reconstructed throughout the treatment fraction. The simplest solution would be to acquire continuous 3D stack-of-stars data during beam-on and reconstruct 4D-MRI epochs that account for short-term variations in respiratory pattern or physiological effects such as organ filling. However, with this approach, the ability to acquire real-time images for instantaneous determination of the current respiratory phase is lost, as is the ability to track or perform respiratory gating based on 2D images.

Radiation therapy systems having a LINAC disposed on an articulated arm have been shown to be advantageous platforms for delivering radiation dose that is highly conformal to a tumor while minimizing dose to the surrounding normal tissue. However, to accurately treat the tumor, the tumor's precise location needs to be determined. In some existing radiation therapy systems with image-guidance, X-ray sources, typically mounted on the ceiling of the treatment room, are used to image the subject. Although these sources can provide real time 2D radiographic images for treatment alignment, they cannot be used to generate clinical images of the subject. In addition, 2D radiographic images lack volumetric information and cannot image tumors with only soft tissue contrast, which in many cases is highly desired.

SUMMARY OF THE DISCLOSURE

The present disclosure addresses the aforementioned drawbacks by providing a system and method for respiratory gated radiotherapy using a respiratory motion model. The motion model can be a continuously updated model that represents a patient's internal anatomy as a mathematical function of an external respiratory surrogate. In one configuration, the model can be implemented on a low-field MRI system, such as a 0.35 T system, using amplitude and velocity of a respiratory bellows as a surrogate. In another configuration, multi-planar model-based respiratory gating can be performed.

In one configuration, a method for magnetic resonance imaging (MRI) guided respiratory gated radiotherapy is provided. The method includes acquiring images of a tissue in a subject and measuring, using the images, a position of the tissue in the images to determine motion of the tissue. A surrogate respiratory signal is acquired contemporaneously with acquiring the images. Motion of the tissue and the surrogate respiratory signal are correlated to create a motion model for the subject. A gated radiotherapy treatment is then administered where the gating is based upon the motion model.

In some configurations, the motion model includes a surrogate respiratory signal and a time derivative of the surrogate respiratory signal. The motion model may be trained using the images prior to correlating motion of the tissue and the surrogate respiratory signal. The motion model may be updated by adding a recently acquired image to the model and/or by removing an earliest acquired image from the motion model. An agreement between gating based upon the motion model and a direct image gating may be determined and gating may be adjusted if a disagreement exists between the motion model gating and the direct image gating. Functional images may be acquired with the images of the tissue and the acquisition of these function images may be interleaved with the acquisition of the tissue images.

In one configuration, a system for performing image guided respiratory gated radiotherapy is provided. The system includes a magnetic resonance imaging system for acquiring images of a tissue in a subject and includes a surrogate respiratory apparatus for generating a surrogate respiratory signal of the subject contemporaneously with the images. A radiotherapy treatment system is also included and is configured to deliver radiotherapy treatment to the subject. A computer system is included and is configured to: i) measure a position of the tissue in the images; ii) determine motion of the tissue using the images; iii) correlate the motion of the tissue and the surrogate respiratory signal using a respiratory motion model; and iv) gate the radiotherapy treatment delivered to the subject using the motion model.

In some configurations the computer system is further configured to train the motion model using the images prior to correlating motion of the tissue and the surrogate respiratory signal. The computer system may be further configured to update the motion model by adding a recently acquired image to the model and removing an earliest acquired image from the model. The computer system may be further configured to determine an agreement between the gating based upon the motion model and a direct image gating. Gating may be adjusted if a disagreement exists between the motion model gating and the direct image gating. The magnetic resonance imaging system may acquire functional images in addition to the images of the tissue and the acquisition of the functional images may be interleaved with the images of the tissue. In some configurations, the surrogate respiratory apparatus may include a bellows device. The magnetic resonance system may also be configured to acquire a stack of adjacent slices in a cyclic sequential fashion, and motion in each slice may be separately correlated to the external surrogate.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

DETAILED DESCRIPTION

A system and method is provided for respiratory gated radiotherapy using a respiratory motion model where MRI-guided respiratory gating is performed with a continuously updated model that represents a patient's internal anatomy as a mathematical function of an external respiratory surrogate. The model represents the patient's internal tissue as if it were to be continuously imaged, such as at a high frame rate, allowing a high signal to noise ratio 3D image to be reconstructed at any breathing phase with magnetic resonance image (MRI). In one configuration, amplitude and velocity of a respiratory bellows acts as the respiratory surrogate. In one configuration, the model is built and updated by fitting anatomical motion measured using MRI images that are periodically acquired at a low frame rate. In another configuration, multi-planar model-based respiratory gating may be performed by sequentially imaging a stack of adjacent slice positions.

Figure 1:
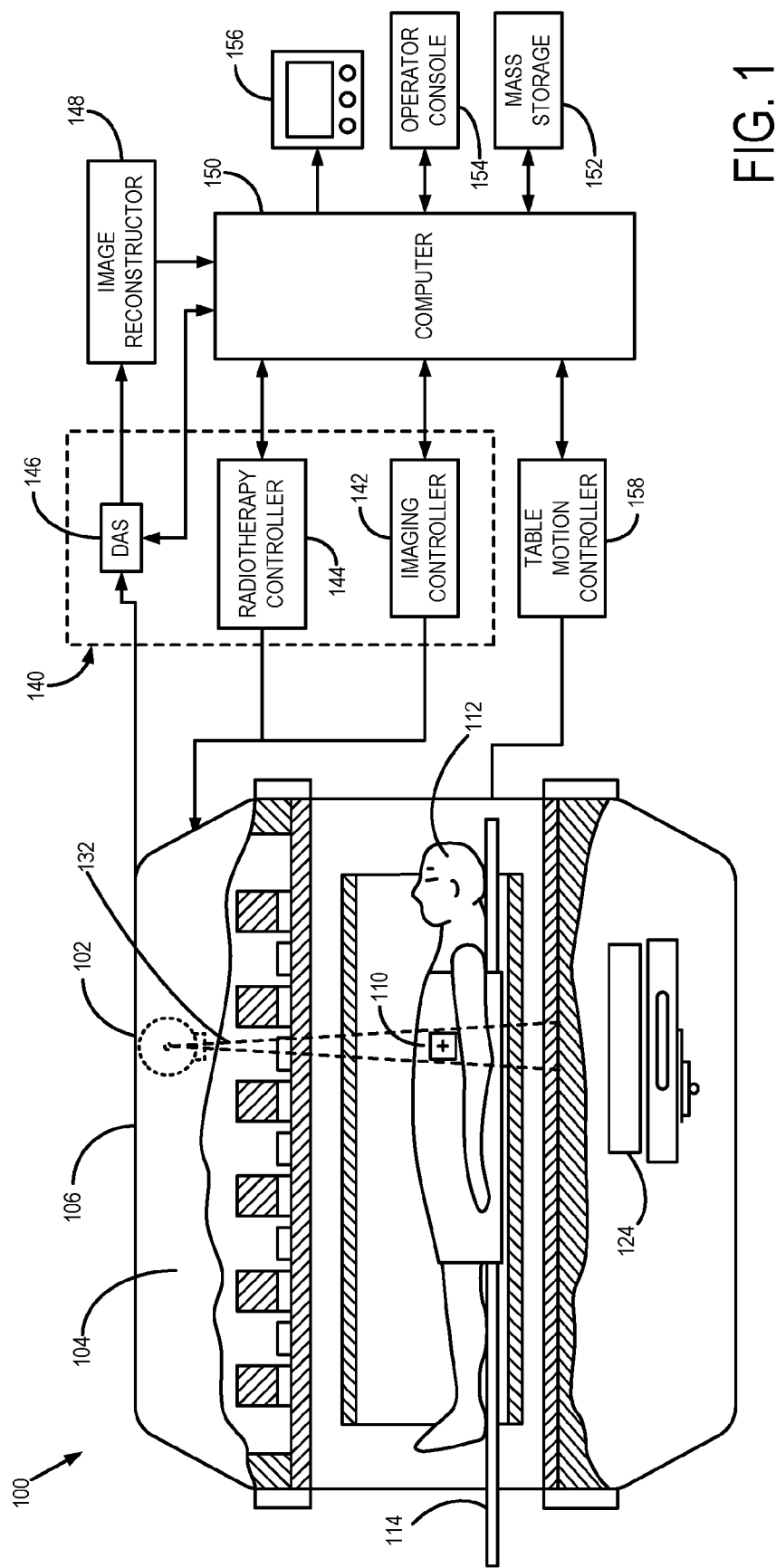
FIG. 1 is a schematic diagram depicting an example imaging-guided radiation therapy system.

The technique can be used to perform MRI-image gated radiotherapy using sequences that do not allow rapid repeated imaging as is required for direct image-based gating, but may provide better image contrast (example: T2-weighted images), or the technique can be used to enable acquisition of MRI functional imaging concurrently interleaved with gated radiotherapy by reducing the frequency of images needed for accurate gating. Functional imaging, such as diffusion-weighted imaging, may be interleaved during gated treatments to assess tumor response. The model may also be used to estimate accumulated dose during a radiotherapy fraction subject to respiratory motion, and/or extract local measures of tissue properties Referring to FIG. 1, a radiation therapy system is depicted which may be used in conjunction with example implementations of the present invention. An example of an image-guided radiation therapy (IGRT) system 100 includes a therapeutic (treatment) source 102 and a diagnostic (imaging) MRI system 104, both of which may be contained in housing 106. The system 100 allows the therapeutic source 102 and the diagnostic MRI system 104 to be focused in a desired manner with respect to a target volume 110 in a subject 112 positioned on a patient table 114.

In some configurations, positioned opposite the treatment source 102 is an optional electronic portal imaging device (EPID), such as x-ray imager detector 124. The detector 124 functions as a portal image device when receiving radiation from the therapeutic source 102. The detector 124 may contain a number of detector elements (e.g., an array of detector elements) that together sense the projected radiation that passes through the subject 112. Each detector element produces an electrical signal that represents the intensity of a beam impinging on that detector element and, hence, the attenuation of the beam as it passes through the subject 112.

The table 114 may allow for moving a subject 112 into and out of the system 100 through use of table motion controller 158. A control mechanism 140 controls the operation of the therapeutic source 102 and the diagnostic system 104. The IGRT system 100 includes an operator workstation 154, which may include a computer 150 that receives commands and scanning parameters from an operator via an input or from a memory or other suitable storage medium 152. The input may be a keyboard, a mouse, a touch screen, or other suitable input mechanism. An associated display 156 allows the operator to observe data from the computer 150, including images of the subject 112 that may be used to review or modify the treatment plan, and to position the subject 112 by way of appropriately adjusting the position of the patient table 114. The operator supplied commands and parameters may also be used by the computer 150 to provide control signals and information to the control mechanism 140.

The therapeutic source 102 is controlled by a radiotherapy controller 144 that forms a part of the control mechanism 140 and which provides power and timing signals to the therapeutic source 102. The controller 140 also provides power and timing signals to the diagnostic imaging system 104 through imaging controller 142. In some configurations, the controller 140 can include two independent controllers for controlling the therapeutic source 102 and the diagnostic imaging system 104, and in other configurations a single controller can control both systems.

The therapeutic source 102 produces a radiation beam 132, or "field," in response to control signals received from the controller 140 focused on a target volume 110. The diagnostic imaging system 104 acquires MR imaging data of the subject 112 for a target volume 110. The position of the patient table 114 may also be adjusted to change the position of the target volume 110 with respect to the therapeutic source 102, the diagnostic imaging system 104, and the detector 124 by way of a table motion controller 158, which is in communication with the computer 150 and operator workstation 154.

A data acquisition system (DAS) 146 samples data from the detector 124. In some configurations, the data sampled from the detector 124 is analog data and the DAS 146 converts the data to digital signals for subsequent processing. In other configurations, the data sampled from the detector 124 is digital data. The operator workstation 154, or a separate image reconstructor 148, receives x-ray data from the DAS 146 and performs image reconstruction. The reconstructed images can be stored in a mass storage device 152, or can be displayed on the display 156 of the operator workstation 154.

Figure 2:
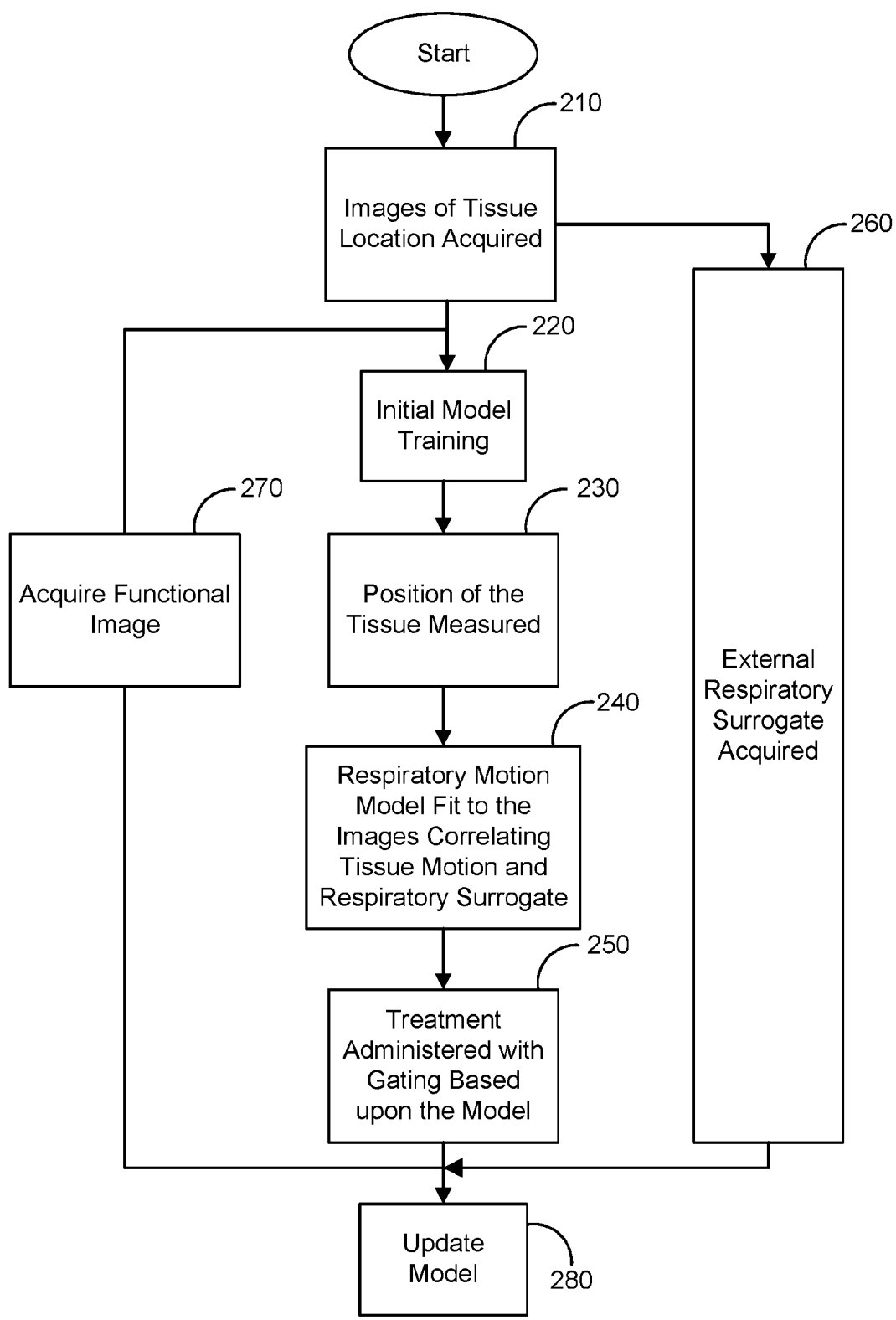
FIG. 2 is a flowchart depicting one configuration of the disclosure.

Referring to FIG. 2, a flowchart depicting one configuration for respiratory gated radiotherapy using a respiratory motion model is shown. The process begins with images of a location of a tumor, lesion, tissue, or anatomy of interest being acquired during a training phase, and are subsequently acquired periodically during gated radiotherapy at step 210. At the same time, an external respiratory surrogate is continuously acquired at 260. A typical time between images would be 2-10 seconds. Initial model training is conducted at step 220. For initial model training, a sequence of N images is acquired. A value of N may be 10, but other values are possible including between 10-100, and the duration of the training period may be about 20-100 seconds. The position of the tumor is measured in each of the N training images at step 230. A patient-specific respiratory motion model is fit to the acquired images at step 240. The model is a mathematical function that establishes a correlation between tissue motion and the respiratory surrogate signal. After the training period, treatment commences and the gating decision is based on the external surrogate, using the model at step 250. The model is updated at step 280. In-between images acquired for model building/updating, functional imaging can be performed depending on time requirements and the functional imaging sequence used and the sequence used for model building/updating.

Figure 3:
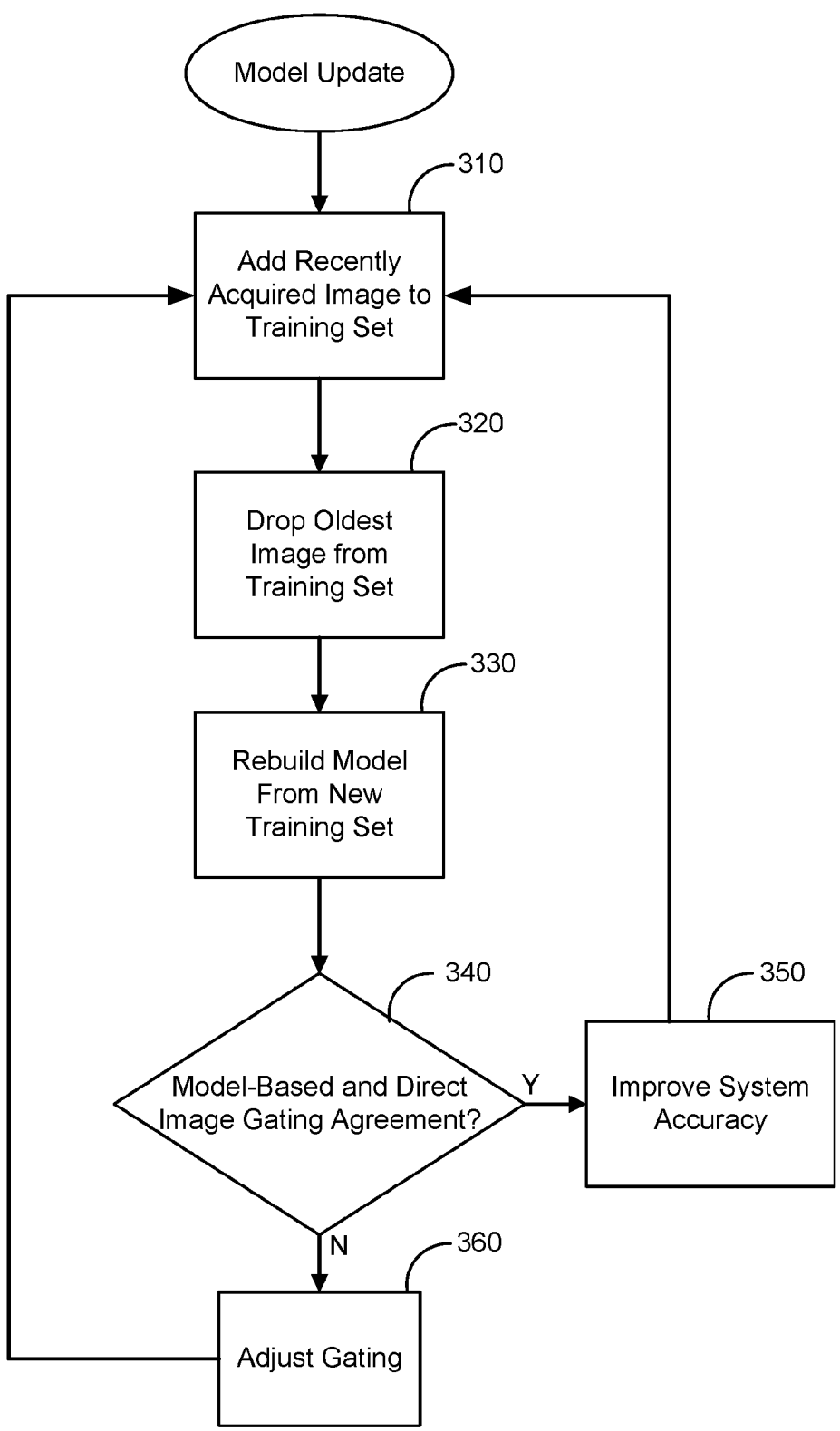
FIG. 3 is a flowchart depicting a model update process that may follow the process of FIG. 2 in some configurations.

Referring to FIG. 3, one configuration for a process of model updating during image guided radiotherapy is depicted. The most recently acquired image is added to the training sequence at step 310, and the earliest acquired image is dropped from the training sequence at step 320. The model is then rebuilt from the new training set at step 330. The model-based gating decision may be compared to the direct image gating decision based on the newly acquired image at step 340. Information on agreement between the model-based and direct image-based gating could be used to trigger an action to improve the accuracy of the system at step 350. In the event of a disagreement between the model-based and direct image-based gating, information may be used to adjust the gating at step 360, such as to pause to avoid an irregular breathing cycle that is not accurately described by the model but was detected via direct imaging. After gating is adjusted at step 360, or after improving the accuracy of the system at step 350, the process may be repeated by returning to step 310. The process may be repeated for the duration of an imaging procedure, the course of a radiotherapy treatment, or for any desired period of time.

Figure 4:
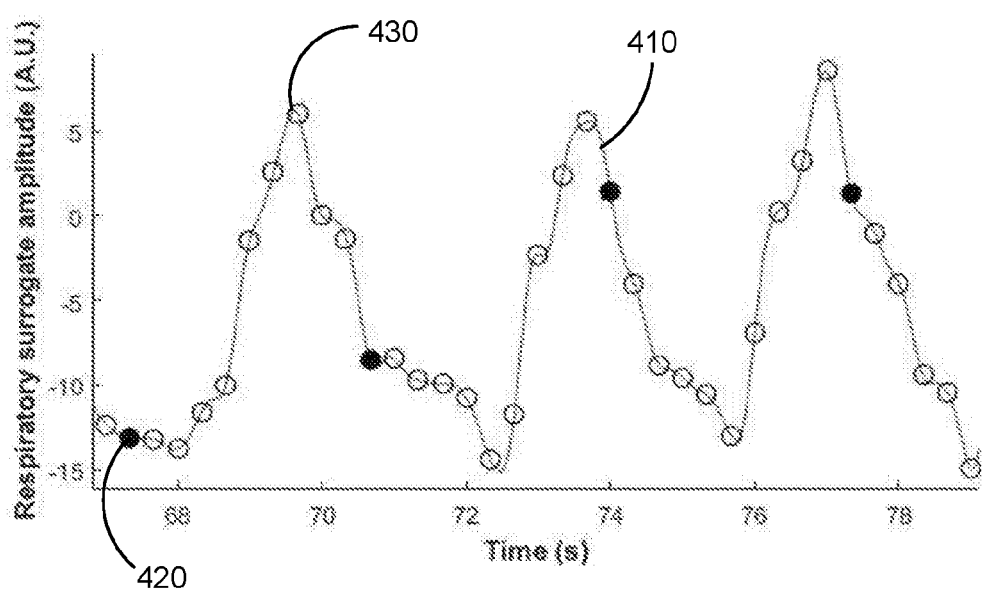
FIG. 4 is a graph representation of an example respiratory surrogate waveform over time.

In one configuration, a high-speed MRI sequence (non-T2 weighted) may be used to acquire sequential images of a subject. In this way, only a fraction of the acquired images may be needed to build the model, allowing the remaining images to be used to assess the model accuracy. Referring to FIG. 4, a respiratory surrogate signal 410 is shown. Images used for model building 420 are reflected as filled-in dots, while images acquired for accuracy assessment 430 are shown as open dots. In one example, the liver of a human volunteer was imaged at a rate of 0.32 seconds between images. A liver vessel was tracked to simulate a tumor. To simulate a T2-weighted image frame rate, only every 10th image was used to build the model. The remaining images were used to evaluate the accuracy of the model-based gating decision. The model in the present example was 94.5% specific compared to ground truth, meaning that over all evaluated image time points, if the model-based gating decision was 'beam-on', the direct image-based gating decision was 'beam-on' 94.5% of the time.

In one configuration, initial model training may consist of 20 images, with a frame rate of 3.2 seconds between images. Deformable image registration may be used to measure the motion of the tumor and surrounding tissue in each training image relative to a breath hold image acquired at the beginning of the session. A simulated tumor contour may be drawn on the reference image and a boundary may be formed by an isotropic margin about the tumor contour. Margins may take on any appropriate size, such as 5 mm about the tumor. A respiratory bellows may be used as the external respiratory surrogate. The bellows may be strapped to the patient's abdomen and a pressure change resulting from abdominal motion may be electronically recorded.

In one configuration, the motion model may take the form of $\vec{x} = \vec{\alpha} V + \vec{\beta} f$, where V is the amplitude of the bellows signal, f is the time derivative of the bellow signal, and $\vec{\alpha}$ and $\vec{\beta}$ are vector-valued tissue-specific parameters extracted using least-squares fitting. During simulated treatment, the motion model may be used to deform the tumor contour to the current breathing phase as determined by the respiratory surrogate. The beam may be turned off if the model-deformed contour is outside the boundary by 10% or more of its area. When an image is acquired, such as every 3.2 seconds, for example, the model may be updated. Then, the model-based gating decision may be compared to the actual image-based gating decision. If the model decision is 'beam-on', but the actual image decision is 'beam-off', a beam veto may be enforced, such as for 1 second, for example. This technique may be used to mitigate the occurrence of irregular breaths that are not accurately described by the model. To evaluate model performance, for the images not used for model building, the model-based gating decision may be compared to the direct image-based gating decision without updating the model.

Figure 5:
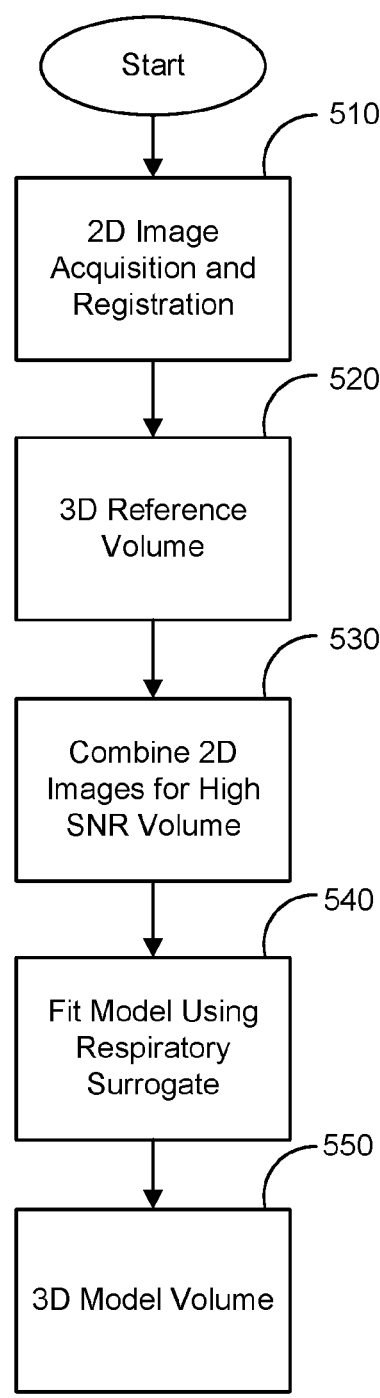
FIG. 5 is a flowchart depicting a creation of a 3D volume based upon an image process of one configuration of the disclosure.

Referring to FIG. 5, a flowchart depicting one configuration of the process of building the respiratory motion model is shown. The surrogate amplitude and velocity may be fit along with the image deformation vectors obtained from a 2D non-rigid image registration to the 5D motion model: $\vec{x} = \alpha v + \beta f + x_0$ where $\vec{x}$ is the estimated tissue position, $\alpha$ and $\beta$ establish a correlation between the surrogate amplitude v and velocity f to the tissue position, and $x_0$ is the initial tissue position. The 2D images are acquired and registered at step 510. A 3D reference volume is acquired using a 3D MR sequence at step 520 during a breath hold. In one example, a 3D reference image may include a 25 sec. balanced steady state free precession (bSSFP) 3D breath-hold sequence with 1.5×1.5×3.0 mm voxel resolution and using deformable image registration via Elastix with bilateral filtering. The 2D images are then combined to form a high SNR volume at step 530, which may have a higher SNR than the 3D reference volume. The model is fit using the respiratory surrogate at step 540. The motion model fit may be a voxel-specific motion model and may be smoothed with a Gaussian kernel to reduce the influence of noise. The 3D model volume is generated at 550.

In some configurations, error evaluation may be performed using leave-one-out landmarks, or with a deformation vector field. This may establish model robustness by providing a user with the agreement or disagreement between different models. Surrogate estimation error may also be analyzed using a cross-validation error routine and the like. Image registration evaluation may also be performed where landmarks may be assessed for how much spatial displacement they experience. 3D deformation using a 2D-3D slice to volume registration may be used to suppress errors, and may also improve registration at sliding tissue interfaces. Accelerated image acquisition may also be performed to reduce over-sampling and decrease the acquisition times.

Figure 6:
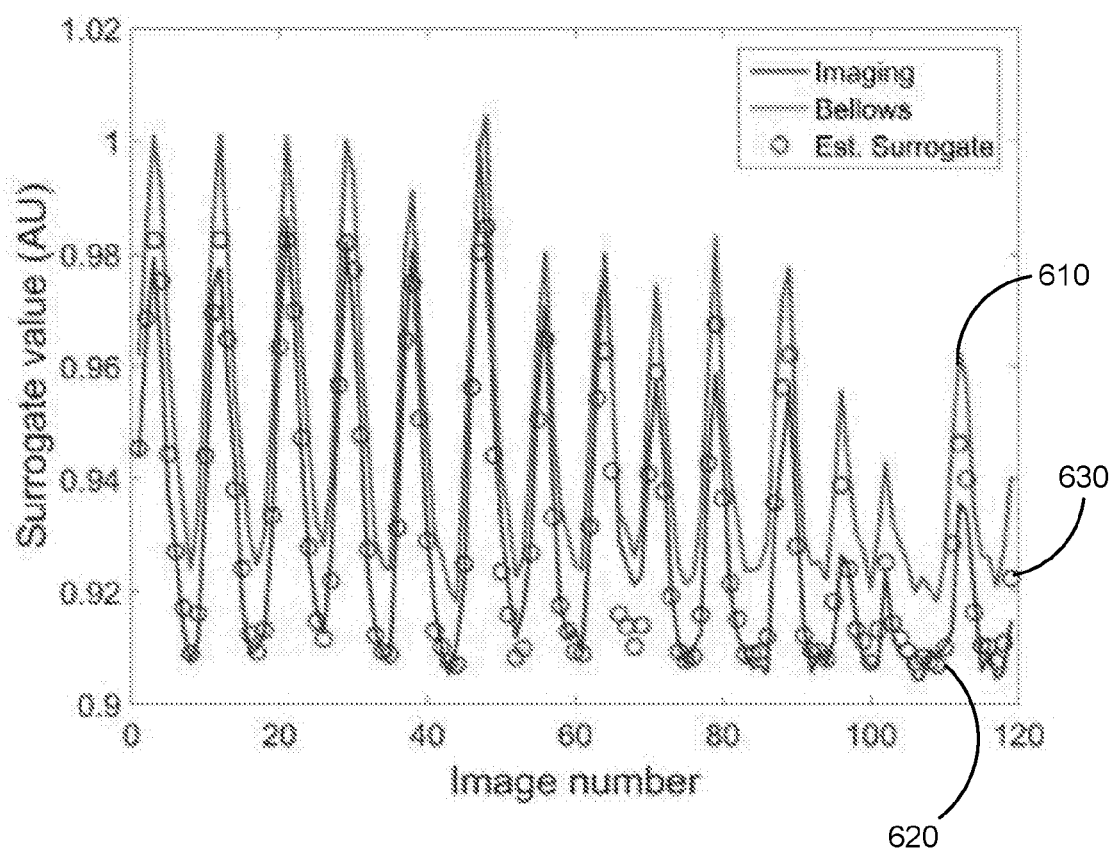
FIG. 6 is a graph representation of example imaging and bellows waveforms.
Figure 7:
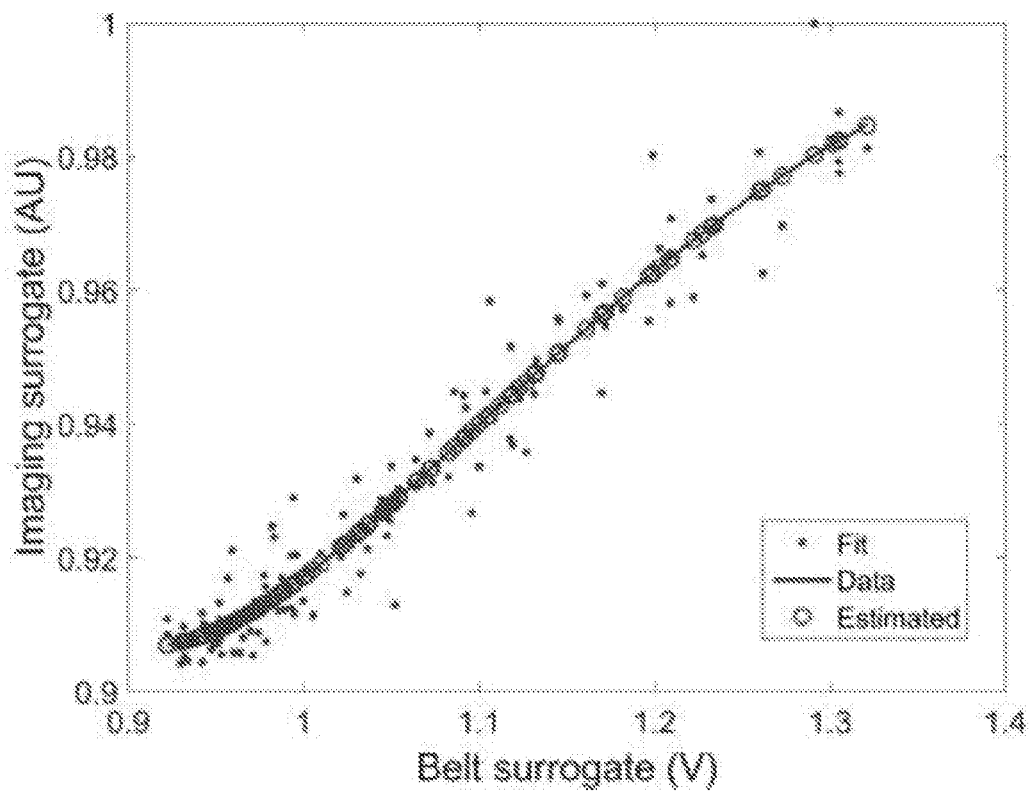
FIG. 7 is a graph representation of an example correlation of the data presented in FIG. 6.

Referring to FIG. 6 one configuration where the respiratory bellows surrogate 610 is correlated to a k-space imaging surrogate 620 derived from a single imaging plane is shown. This correlation allows the imaging surrogate to be estimated using the bellows surrogate while imaging at different lateral planes, as shown with estimated points 630. This technique will allow the model to be constructed with an imaging based surrogate that may more accurately model anatomical motion, and would be accessible during radiotherapy gating. Referring to FIG. 7, a correlation between the imaging and bellows surrogates is shown with example data.

Figure 8:
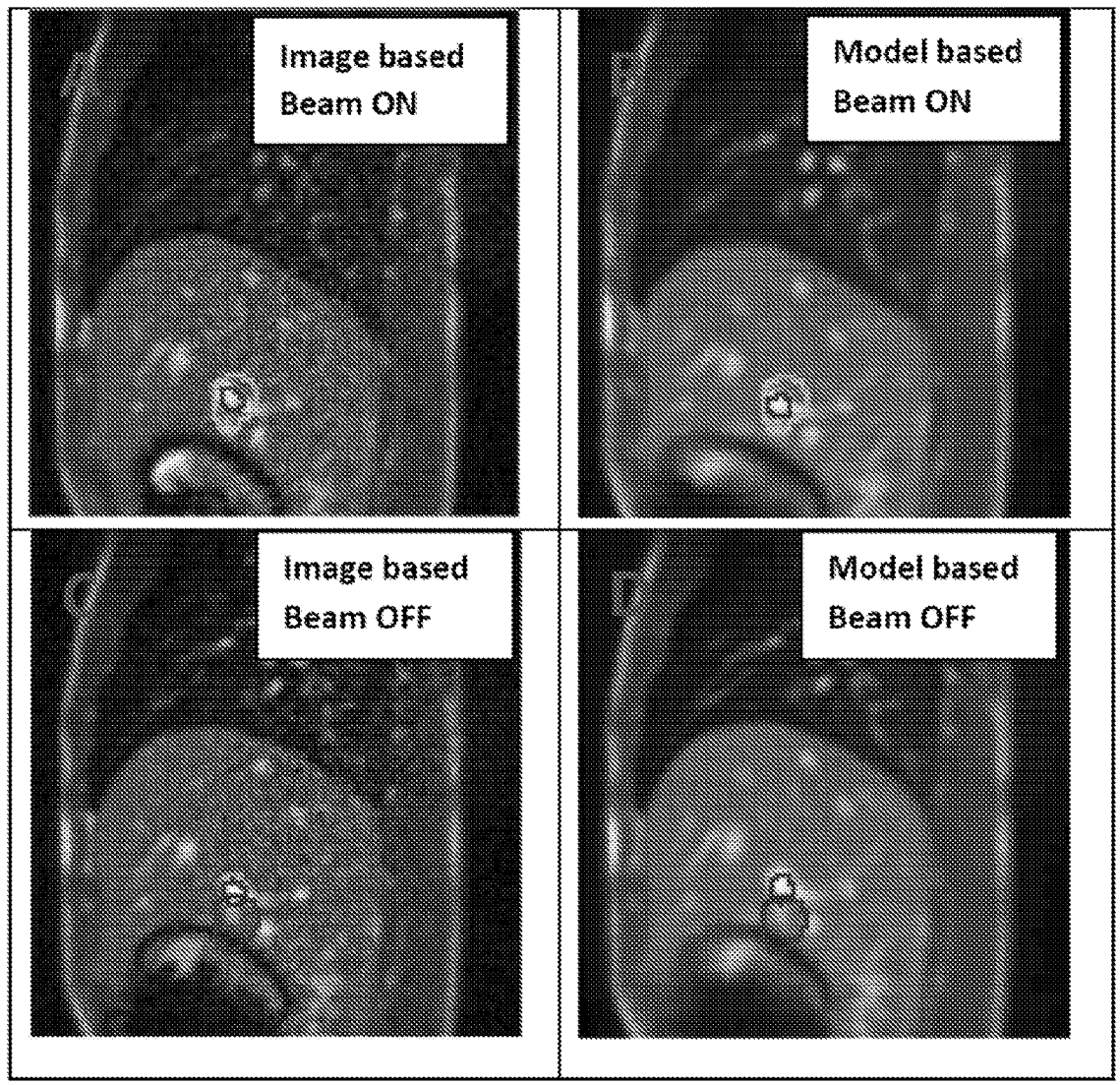
FIG. 8 is an example image set depicting some configurations when a radiotherapy treatment beam is on and off.

Referring to FIG. 8, in one configuration the radiotherapy treatment beam may be turned off if the model-deformed contour is outside the boundary by a predetermined amount, such as 10% or more of its area. Examples are shown in FIG. 8 of: raw image and image-based gating decision 'beam-on' is shown in the upper left, model-based image and model-based gating decision 'beam-on' is shown in the upper right, raw image and image-based gating decision 'beam-off' is shown in the lower left, and model-based image and image-based gating decision 'beam-off' is shown in the lower right.

In another configuration, multi-planar model-based respiratory gating may be performed. Clinical MRI-based respiratory gating is performed with single sagittal plane images only, because imaging in multiple planes is not fast enough to turn the beam off in time to accommodate respiratory motion with current MRI technology. This is a significant limitation because for some tumor types, the spatial relationship of the tumor and nearby radio-sensitive normal organs is complex and dynamic and therefore not easily captured by single plane imaging. For example, pancreatic tumors are adjacent to the stomach and wrapped by the duodenum, organs which are very sensitive to high radiation doses and which move and deform with respiration as well as digestive processes.

The multi-planar model-based approach overcomes the imaging speed limitation on multi-plane imaging by sequentially imaging a stack of adjacent slice positions. These raw images cannot be used directly for gating because the anatomy they represent is inconsistent image-to-image until the entire stack has been imaged and the sequence starts again with a period of a few seconds. In one configuration, a motion model is used to interpolate a virtual image at every slice position at all times when a raw image is not available.

The present disclosure has described one or more preferred embodiments, and it should be appreciated that many equivalents, alternatives, variations, and modifications, aside from those expressly stated, are possible and within the scope of the invention.

The invention claimed is:

1. A method for magnetic resonance imaging (MM) guided respiratory gated radiotherapy, comprising:
    acquiring images of a tissue in a subject;
    measuring, using the images, a position of the tissue in the images to determine motion of the tissue;
    acquiring a surrogate respiratory signal contemporaneously with acquiring the images;
    correlating motion of the tissue and the surrogate respiratory signal to create a motion model for the subject administering a gated radiotherapy treatment wherein the gating is based upon the motion model, and updating the motion model throughout the gated radiotherapy treatment.

2. The method of claim 1 wherein the motion model includes a surrogate respiratory signal and a time derivative of the surrogate respiratory signal.

3. The method of claim 2 wherein the motion model is of the form:

$$\vec{x} = \vec{\alpha} V + \vec{\beta} f$$

where $\vec{x}$ represents an estimated tissue position, V is the amplitude of a bellows signal, f is the time derivative of a bellows signal, and $\vec{\alpha}$ and $\vec{\beta}$ are vector-valued tissue-specific parameters.

4. The method of claim 2 wherein the motion model is a 5D motion model of the form:

$$\vec{x} = \alpha v + \beta f + x_0$$

where $\vec{x}$ represents an estimated tissue position, a and represent a correlation between a surrogate signal amplitude v and a velocity f to the tissue position, and $x_0$ represents an initial tissue position.

5. The method of claim 1 further comprising training the motion model using the images of the tissue prior to correlating motion of the tissue and the surrogate respiratory signal.

6. The method of claim 1 where updating the motion model includes using a recently-acquired image of the tissue of the subject.

7. The method of claim 6 further comprising removing an earliest acquired image from the motion model when updating the motion model.

8. The method of claim 6 further comprising determining an agreement between gating of the gated radiotherapy treatment using the motion model and a direct image gating.

9. The method of claim 8 further comprising adjusting gating of the gated radiotherapy treatment upon determining a disagreement between the motion model gating and the direct image gating.

10. The method of claim 1 further comprising acquiring functional images of the tissue of the subject.

11. The method of claim 10 wherein acquiring the functional images includes interleaving acquisition of the functional images with the acquisition of the images of the tissue.

12. A system for performing image guided respiratory gated radiotherapy, comprising:
    a magnetic resonance imaging system for acquiring images of a tissue in a subject;
    a surrogate respiratory apparatus for generating a surrogate respiratory signal of the subject contemporaneously with acquiring the images of the tissue;
    a radiotherapy treatment system configured to deliver radiotherapy treatment to the subject;
    a computer system configured to:
        i) measure a position of the tissue in the images;
        ii) determine motion of the tissue using the images;
        iii) correlate the motion of the tissue and the surrogate respiratory signal using a respiratory motion model;
        iv) gate the radiotherapy treatment delivered to the subject using the motion model; and
        v) update the motion model throughout radiotherapy treatment.

13. The system of claim 12 wherein the motion model includes a surrogate respiratory signal and a time derivative of the surrogate respiratory signal.

14. The system of claim 13 wherein the motion model is of the form:

$$\vec{x} = \vec{\alpha} V + \vec{\beta} f$$

where $\vec{x}$ represents an estimated tissue position, V is the amplitude of a bellows signal, f is the time derivative of a bellows signal, and $\vec{\alpha}$ and $\vec{\beta}$ are vector-valued tissue-specific parameters.

15. The system of claim 13 wherein the motion model is a 5D motion model of the form:

$$\vec{x} = \alpha v + \beta f + x_0$$

where $\vec{x}$ represents an estimated tissue position, a and represent a correlation between a surrogate signal amplitude v and a velocity f to the tissue position, and $x_0$ represents an initial tissue position.

16. The system of claim 12 wherein the computer system is further configured to train the motion model using the images prior to correlating motion of the tissue and the surrogate respiratory signal.

17. The system of claim 12 wherein the motion model is updated by adding a recently-acquired image to the model and removing an earliest acquired image from the model.

18. The system of claim 17 wherein the computer system is further configured to determine an agreement between the gating based upon the motion model and a direct image gating.

19. The system of claim 18 wherein the computer system is further configured to adjust gating upon determining a disagreement between the motion model gating and the direct image gating.

20. The system of claim 12 wherein the magnetic resonance imaging system is further configured to acquire functional images in addition to the images of the tissue.

21. The system of claim 20 wherein the magnetic resonance imaging system is configured to acquire functional images and the images of the tissue according to an interleaved acquisition.

22. The system of claim 12 wherein the surrogate respiratory apparatus includes a bellows.

23. The system of claim 12 wherein the magnetic resonance system is configured to acquire a stack of adjacent slices in a cyclic sequential fashion, and motion in each slice is separately correlated to the external surrogate.

* * * * *

UNITED STATES PATENT AND TRADEMARK OFFICE
CERTIFICATE OF CORRECTION

PATENT NO. : 11,617,903 B2
APPLICATION NO. : 16/634308
DATED : April 4, 2023
INVENTOR(S) : James M. Lamb et al.

It is certified that error appears in the above-identified patent and that said Letters Patent is hereby corrected as shown below:

In the Claims

Column 9, Claim 1, Line 12, "(MM)" should be --(MRI)--.

Signed and Sealed this
Twenty-seventh Day of June, 2023

Katherine Kelly Vidal
*Director of the United States Patent and Trademark Office*